US008724871B1

(12) United States Patent
Biagiotti et al.

(10) Patent No.: US 8,724,871 B1
(45) Date of Patent: May 13, 2014

(54) METHOD AND SYSTEM FOR IDENTIFYING ANOMALIES IN MEDICAL IMAGES (71) Applicants: ATTI International Services Company, Inc., Hauppauge, NY (US); Eli Levi, Dix Hills, NY (US)

(72) Inventors: William Biagiotti, St. James, NY (US); Eli Levi, Dix Hills, NY (US); David Levi, Ventnor City, NJ (US)

(73) Assignee: ATTI International Services Company, Inc., Hauppauge, NY (US)

( * ) Notice: Subject to any disclaimer, the term of this patent is extended or adjusted under 35 U.S.C. 154(b) by 0 days.

(21) Appl. No.: 13/628,167

(22) Filed: Sep. 27, 2012

Related U.S. Application Data (60) Provisional application No. 61/570,474, filed on Dec. 14, 2011.

(51) Int. Cl.
G06K 9/00 (2006.01)
(52) U.S. Cl.
USPC ........... 382/128; 382/130; 382/132; 382/133; 382/218; 382/224
(58) Field of Classification Search
USPC .......................... 382/128, 130–133, 218, 224
See application file for complete search history.

(56) References Cited

U.S. PATENT DOCUMENTS

| 5,642,431 | A | * | 6/1997 | Poggio et al. ............ 382/118 |
| 6,032,678 | A | | 3/2000 | Rottem |
| 6,650,766 | B1 | | 11/2003 | Rogers et al. |
| 7,162,062 | B2 | | 1/2007 | Breitenstein et al. |
| 7,899,514 | B1 | | 3/2011 | Kirkland et al. |
| 8,165,380 | B2 | | 4/2012 | Choi et al. |
| 2002/0064788 | A1 | | 5/2002 | Monforte |
| 2003/0007598 | A1 | | 1/2003 | Wang et al. |
| 2003/0231790 | A1 | | 12/2003 | Bottema |
| 2009/0129639 | A1 | | 5/2009 | Ortega et al. |
| 2010/0017225 | A1 | | 1/2010 | Oakley et al. |
| 2011/0015942 | A1 | | 1/2011 | Oakley et al. |

* cited by examiner

Primary Examiner — Ruiping Li
(74) Attorney, Agent, or Firm — Brian Roffe (57) ABSTRACT Method and sequence for locating anomalous features in medical images in which medical images are supplied by an external source such as a CAT or XRAY scan machine or other similar device. A sequence of specific measurements is executed on the supplied data to obtain metrics relating to the images. The metrics are then compared to the corresponding values in an accompanying database resulting in an anomalous/not anomalous determination. Anomalous determinations are presented to the test operator for final analysis along with supplemental historical data. In application to all types of medical imagery, potential anomalies are quickly located resulting in an efficient and more accurate diagnosis.

33 Claims, 6 Drawing Sheets

| Primary Category | Components | Secondary Components |
|---|---|---|
| Head | Brain | Frontal Lobe |
| | | Parietal Lobe |
| | | Temporal Lobe |
| | Nasal | Sinuses |
| | Optic System | Eyes |
| | | Optic nerve |
| | Otic System | Ear drum |
| | | Eustachian tube |
| | | |
| Torso | Organs | Heart |
| | | Lungs |
| | | Liver |
| | | Breasts |
| | | Intestines |
| | Muscle | |
| | Skeletal Structure | Spine |
| | | Ribs |
| | Circulatory System | Veins |
| | | Arteries |
| | | |
| Extremities (Limbs) | Arms | Skeletal structure |
| | | Muscle |
| | | Circulatory System |
| | | |
| | Legs | Skeletal structure |
| | | Muscle |
| | | Circulatory System |

FIGURE 1: Example of Database Organization (excluding metrics)

| Secondary Components | Entry Number | Analytical Information | Entry N: Metrics |
|---|---|---|---|
| Parietal Lobe | 1 | Patient Age | Intensity range ratio |
| | | Patient Sex | Passing threshold for intensity range ratio comparison |
| | | Area of anomaly | Intensity range positioning |
| | | Shape of anomaly | Intensity density ratio |
| | | Additional medical testing performed with test results. | |
| | | Diagnosis/Prognosis | Passing threshold for intensity density ratio comparison |
| | | Treatment | Intensity density positioning |
| | | Outcome | |
| | | Time to resolution | |
| | 2 | Entry 2 (information as above) | (metrics for entry 2) |
| | 3 | Entry 3 (information as above) | (metrics for entry 3) |
| | 4 | Entry 4 (information as above) | (metrics for entry 4) |
| Temporal Lobe | 1 | Entry 1 (information as above) | (metrics for entry 1) |
| | | | |

FIGURE 2: Subset of database organization with metric entries

FIGURE 3 - Flowchart of Analysis Sequence

FIGURE 4 - Continuation of Analysis Sequence

METHOD AND SYSTEM FOR IDENTIFYING ANOMALIES IN MEDICAL IMAGES

CROSS-REFERENCE TO RELATED APPLICATION

This application claims priority under 35 U.S.C. §119(e) of U.S. provisional patent application Ser. No. 61/570,474 filed Dec. 14, 2011, which is incorporated by reference herein.

FIELD OF THE INVENTION

The present invention relates generally to the field of medical imaging and measurement as facilitated by medical instrumentation applying technologies including but not limited to electroencephalography (EEG), Magneto Encephalography (MEG), Electrocardiography (EKG), Positron Emission Tomography (PET), X-Ray Computed Tomography (CT), Magnetic Resonance Imaging (MRI) and numerous other technologies used in the medical field. Specifically, the present invention relates to a method comprising an operational sequence of steps to mine statistical data from historical medical images creating a database of metrics, and separately or in combination therewith, using automated software methods (algorithms) to guide the interpretation of new medical images by intelligently comparing specific metrics on regions of interest in the new medical images potentially containing a high probability of anomalous characteristics to selected metrics from the database.

The present invention also relates to methods, systems, arrangements, apparatus and computer programs that receive and/or analyze electronic medical signals for one or more anomalous features, and enable at least one responsive action based on the presence and/or absence of an anomalous feature or features in the electronic medical signals being received and analyzed.

The present invention further relates to methods, systems, arrangements, apparatus and computer programs for utilizing a database repository of images and/or signals to which test images and/or signals and/or portions thereof, obtained using medical technology applications such as those listed above, can be analyzed relative to or compared to on the basis of normal and/or anomalous tissue composition.

BACKGROUND OF THE INVENTION

For the purposes of the following description, reference will be made to the terms 'body components' and 'body parameters'. These terms are interchangeable with the terms 'organs', 'bones' or any other body part associated with, but not limited to, humans or any other living creature. Reference will also be made to the terminology of 'anomaly' or 'anomalies'. These terms are interchangeable with 'cancer', 'tumor', 'growth' or any other negative classification of a physical presence or condition within a living body. Furthermore, reference will be made herein to the term "image". This term is to be considered for the present description interchangeable with 'visual image', 'audible sound waveform', 'X vs. Y. data plot' or any other stored data terminology. Also, whenever the term "image" is used, unless indicated to the contrary, it also includes the entirety of signals necessary to depict it. This is appropriate because images can be reduced to signals via appropriate signal processing hardware and/or software.

Medical imaging equipment for the testing and/or measurement of internal and/or external body parameters is known. Enormous quantities of medical images exist which were produced for patients seeking diagnosis of health issues and maladies. The content of these images can be summarily categorized as:

a) Body structures which present as normal (i.e., "healthy").

b) Body structures which present, or are suspected to present, physical anomalies, including but not limited to, cancers, tumors, growths, diseases or other conditions (which manifest as changes in normal tissue), and other abnormal structures.

This invention targets the images in category (b), those with physical anomalies present or suspected.

Depending upon the body component that is being analyzed, there are many recording and imaging technologies that can be employed to acquire the present conditional state of that body component, or that have already been employed to acquire the state of the body component. Such medical equipment will be acquiring and recreating internal imagery in the form of electronic data (waveforms). A commonality of all of these technologies is that there is a requirement, or at least a desire, to analyze the acquired data to determine if there are any pathological or anomalous features that warrant further analysis, investigation, testing or other action.

Analysis or interpretation of this data usually requires highly skilled personnel, such as a radiologist. It is often the responsibility of such personnel to identify any pathological and/or anomalous features. In medical imagery, anomalous features can usually be visually identified by radiologists because for example, they either contain higher intensity values (brighter) or lower intensity values (darker) than the surrounding features within the image.

There is a growing effort to shift the burden of image analysis away from purely manual methods toward machine-assisted methods in order to improve the efficiency and accuracy of reported results. Manual visual analysis is inherently subject to inconsistency because it is highly dependent upon the skill of the individual tasked with the analysis. The accuracy of the analysis across the spectrum of radiologists, or other medical personnel reviewing images, is variable, manifesting in an unacceptable rate of false negatives and false positives. Manual visual analysis relies on a sequence of imperfect technological operations and devices. Once a medical image has been produced by the imaging instrumentation, the image data typically goes through a process involving data reduction, video signal image generation, visual image generation and human visual perception. The process of generating the video image for the radiologist to analyze relies heavily upon the ability of supporting electronic equipment to produce an accurate visual depiction of the image data. Frequently, such equipment is either incapable of such accuracy or is not properly maintained by the operator. The majority of medical image viewing is accomplished with commercial-grade computer monitors which is only adequate for non-critical applications. It is ill advised to utilize these mass-produced monitors in critical viewing applications, such as radiology, as they will introduce undesirable analysis issues. For example, resolution reduction will be required to view the entire image on a commercial monitor, the monitor's panels have uncalibrated image grayscale (contrast) performance, and non-uniform image quality across the display surface and also between otherwise identical monitors. Medical grade monitors, which are calibrated for critical imaging, also introduce issues such as presenting so much resolution across a very large viewing area, that repetitive manual analysis is fatiguing. Erroneous conclusions resulting from this analysis may result in improper treatment or, worse yet, no treatment at all for life-threatening conditions.

The goal of machine-assisted image analysis methods is to maximize the accuracy of the reading of the images by taking the monochrome (grayscale) image (data bitmap) generated by the medical instrument, analyzing the contents of the image and intelligently highlighting any regions which present as suspicious and/or abnormal so that a radiologist can make a more reliable and consistent diagnosis. In a sense, the images are filtered for review by the radiologist. The benefit of these methods is that they are projected to be far more consistent and comprehensive when compared to present entirely manual inspection.

Machine-assisted image analysis methods are known, but often lack the degree of artificial intelligence necessary to guide the processing sequence to search for both recognizable anomalies and historically possible anomalies.

Therefore, there exists a need for an automated method, arrangement, system, apparatus and computer program which encompass the ability to identify and/or present anomalies which human inspection would normally find, and in addition, to identify and/or present anomalies which human inspection would not normally find, but are historically present. The invention, described below, is directly applicable to these requirements.

SUMMARY OF THE INVENTION

A method in accordance with the invention comprises an operational sequence of steps to mine statistical data from historical medical images creating a database of metrics and using automated software methods (as implemented in a software program embodied on computer-readable media and executed by a computer containing a processor and operating hardware and software), and guide the interpretation of new medical images by intelligently comparing specific metrics from the database in one or more regions of interest containing a high probability of anomalous characteristics. The steps are performed by the processor that executes the software, and is controlled by a user via one or more user interfaces.

The software program will receive as input, an electronic image (picture) of a component of the body, which by definition contains intensity information (grayscale values) relative to its physical location. Segmentation methods implemented by the software program will isolate one or more regions of interest from structural content within the received image and primary processing will measure characteristics and consistency of the image inside those regions of interest and then by reference, compare those metrics to previously determined and accepted metrics gathered from anomalies within the database. The database metrics are derived from the historical medical images.

If the region of interest of the component under scrutiny contains characteristics consistent with an entry that was documented in the database (and thus containing measured values that are known to represent the presence of a cancer, tumor, growth, a disease which presents an abnormal internal structure, or other anomaly), the algorithmic analysis will identify that region as an anomaly.

Finally, in the event of detection of an anomaly, the invention will preferably present the original image on a computer monitor or other display device and visually highlight, or otherwise indicate, the anomalous region. If available from the database, further details about the anomalous region may also be presented.

BRIEF DESCRIPTION OF THE DRAWINGS

A more complete appreciation of the present invention and many of the attendant advantages thereof will be readily understood by reference to the following detailed description of the invention when considered in connection with the accompanying drawings in which.

DETAILED DESCRIPTION OF PREFERRED EMBODIMENTS

To fulfill the goal of a machine-aided medical image diagnostic tool, the present invention incorporates a categorized metric database with data mined and calculated from historical images using a novel combination of manual steps and of equal or greater importance, computer-implemented algorithmic operations, in which the categorized database is then used in a comparison sequence implemented within a software program designed to achieve results not consistently achievable with conventional radiological analysis. There are no implied limitations as to where the software program may exist and be executed, so it may reside within a wide range of appliances such as conventional computers, embedded within medical instrumentation or even as firmware within a microprocessor, DSP, or FPGA device. There is also no implied restriction as to which computer language that the software is created in.

Figure 1:
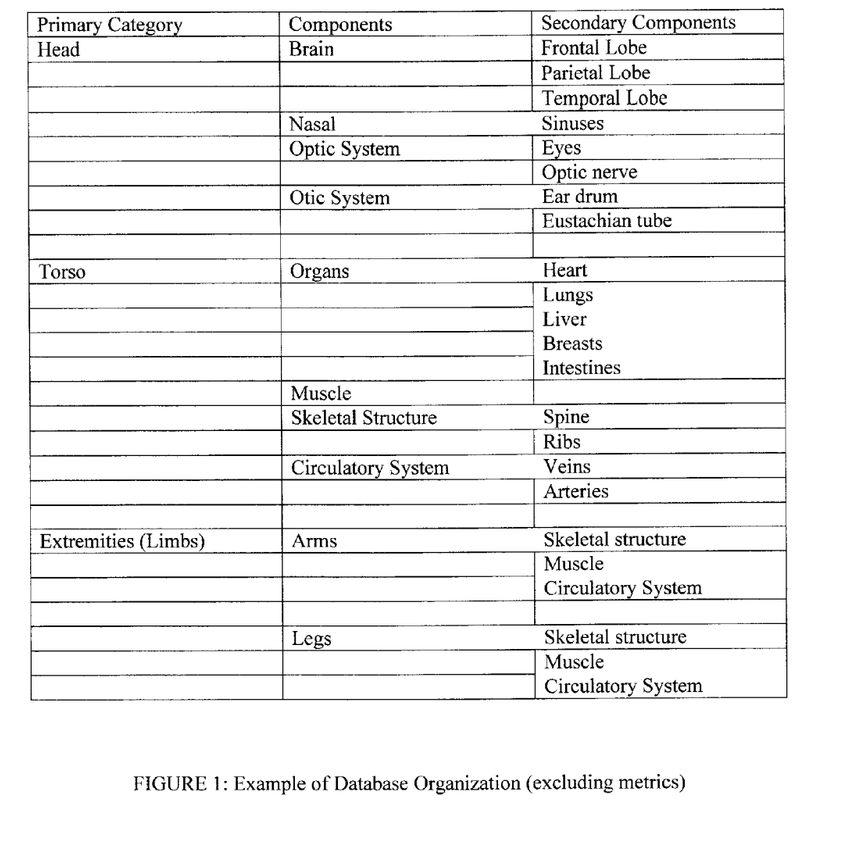
FIG. 1 shows a subset of the database organization in accordance with the invention.
Figure 2:
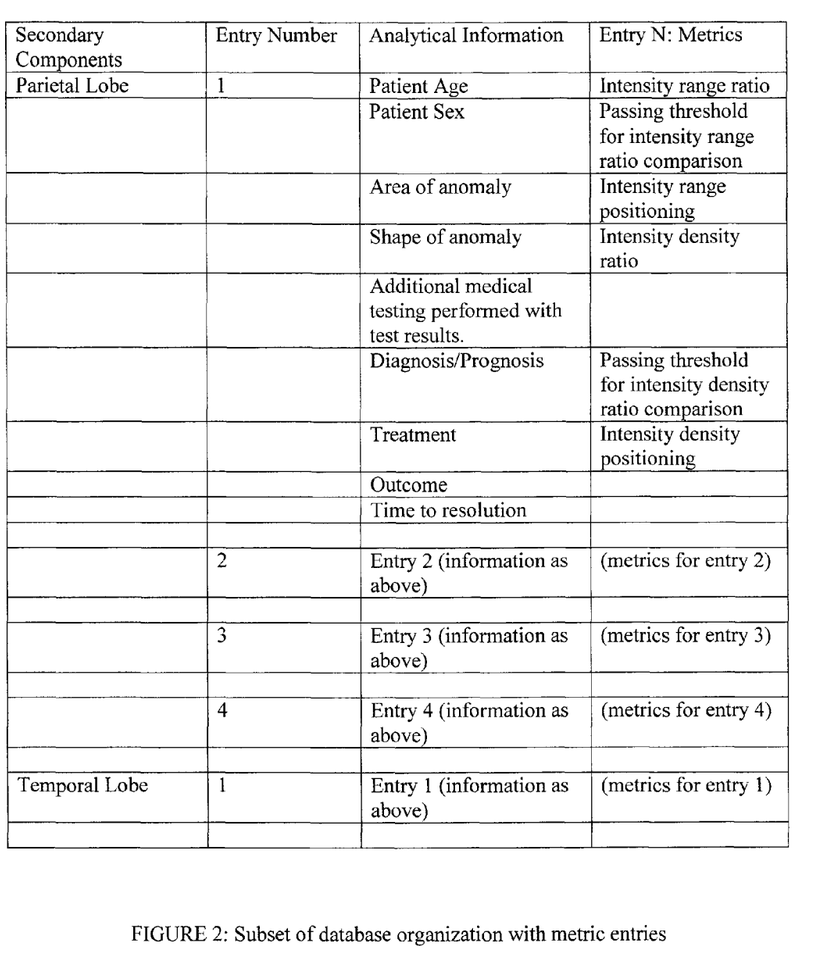
FIG. 2 shows a subset of the database organization with metric entries.

A foundation of the invention is the creation of a database 10 of metrics derived from historical medical images (see FIGS. 1 and 2). This database 10 may be created using a database creation program (a software interface and algorithm) running on a computer at one site from information obtained from one or a plurality of different sites. The information may be provided from each data gathering site to the database creating program by a direct coupling or through a wireless network, or any other data connection. The physical structure of the database 10 is known to those skilled in the art. Ideally, the database 10 should be secured, backed-up and tamper-proof.

The method of incorporating historical medical images into the database 10 starts with the determination of the format of the original images. If the images are in 'hard-copy' form (such as photographic film, transparency, etc.), a preferred operation is to electronically photo scan each image and convert it into a digital file that is compatible with a software interface and algorithm, which scanning and conversion can be by any known technique. If the image is already in electronic (digital) form, it is only necessary to convert the digital file into a file format that is recognized by the software algorithm in a common procedure known to those skilled in the art. Preferred embodiments of the invention will recognize the majority of industry-standard lossless file formats such as, but not limited to, BMP, DICOM, PNG, and RAW. All file formats are encompassed within the scope of the invention.

To process the image, manual and/or automatic segmentation methods are preferably utilized to, first, delineate at least one targeted area (i.e., human organ or similar) in the original image if the original image contains content that is excessive (i.e., surrounding structure) and not directly applicable to the computations and second, to identify the region where the anomaly solely exists. The result of this delineation is the targeted organ with further delineation showing the separation between the anomaly and the surrounding healthy tissue. As an overview of one implementation of this process, a computer program that would achieve this would be programmed to enable a user to utilize a user interface to delineate one or more targeted areas and then initiate a routine, e.g., by selecting a designated region on the display on which the targeted area is displayed, to identify the region where the anomaly exists.

More specifically, in one embodiment of the invention, the delineation (also referred to as segmentation) will be handled manually by a human operator who will draw a boundary line around these structures using an electronic device such as a pen tablet or computer mouse while viewing the original image on a computer monitor or other display device. The invention does not limit this step to be a manual process and those skilled in the art will understand that it is possible to employ automated methods to achieve similar results.

In another embodiment of this invention, the total area of the historical images that are analyzed and saved to the database would be minimized in order to realize higher performance through a reduction in execution time and database size. That is, the execution time and database size obtained after minimizing the total area of the historical images is highly likely to be less than the execution time and database size if the total area of the historical images is not minimized, and thus system performance is improved.

The maximum area of the historical images utilized would be defined to only be a minimal percentage larger than each diagnosed anomaly in those images as delineated by manual or automatic methods: the percentage being about ten (10) percent in preferred embodiments. The shape of the new outside image boundary would be contoured to follow the shape of the inner anomaly to ensure that enough valid 'good' tissue remains around the periphery of the anomaly for proper metric analysis. The reduction in area around the outside of the anomaly serves to increase operational efficiency by reducing redundant analysis of healthy tissue and should have no meaningful impact upon the calculated metrics discussed below. Since the database is projected to contain a very large number of historical image entries and associated metrics, a reduction in size of each stored historical image would greatly reduce the memory requirements of the database.

Using the delineated boundaries for anomalous and normal tissue, software algorithms will examine the intensity levels in the existing medical images and calculate or otherwise determine one or more suitable metrics, including but not limited to the metrics listed below.

A first metric is the ratio of the intensity range (brightness) of the (historical database's) anomalous tissue (as delineated by, for example, manual input) relative to surrounding healthy tissue within the same image. The ratio of the two parameters would be calculated as the intensity range of anomaly divided by the intensity range of surrounding normal tissue and is a dimension-less quantity.

Image brightness is represented digitally in the image data file by a binary code for each dot or pixel within a range of 0 to 255 in a medium resolution 8 bit system and 0 to 4095 in a high resolution 12 bit system. Typically, a larger code represents a brighter dot or pixel at that specific location.

The term 'intensity range' is defined, for the purposes of the description herein, as those pixels or dots having an intensity between about 10 percent and about 90 percent of the overall range of intensities of the target structure. This range may vary based on, for example, the specific manner of construction and use of the invention. Utilizing the intensity ratio, rather than the absolute intensity values, uniquely bypasses the problem of image normalization. Image normalization would traditionally be required to compensate for medical instrument calibration variations in order that images from different sources could be compared. The deletion of this step results in a more efficient sequence. As such, a significant improvement is obtained at this stage of the invention when forming the database 10 in that image normalization is not required.

As a supplemental metric to the image intensity range, the positioning of the normal and anomalous intensity ranges to each other is categorized as either 'over' (anomaly brighter than normal tissue), 'overlapping brighter' (anomaly brighter than normal tissue but overlapping into normal tissue range), 'within' (anomaly occupies same intensity range as normal tissue), 'overlapping darker' (anomaly darker than normal tissue but overlapping into normal tissue range), or 'under' (anomaly darker than normal tissue). This metric will be recorded into the database for each image in association therewith. Other categories may also be provided depending on, for example, the images.

A second metric is the ratio of the local intensity density of anomalous tissue relative to the intensity density of surrounding healthy tissue within the same image. The ratio of the two would be calculated as the intensity density of the anomaly divided by the intensity density of the surrounding normal tissue and is a dimension-less quantity. The invention uses the measurement of variance to quantify intensity density. Known to those skilled in the art to which this invention pertains, by definition, the variance is a measure of how far a set of numbers (in this case, intensity values) are spread out from each other.

Anomalous structures of the sort that are targeted by this invention are known to have intensity densities that are numerically different from that of the 'normal' tissues around it. In a visual examination of a medical image by a radiologist, the subtlety of the intensity density difference has a probability of being below the threshold of what the human eye can perceive reliably.

Application of the measure of variance as a determining metric ensures that the relationship of pixel intensity values relative to others within a delineated grouping is examined and is a factor in the final comparison. Those skilled in the art would recognize that histograms and correlation coefficients may be utilized when comparing intensity statistics from different sources. Those processes also require image normalization and inherently, the combination of those processes are computationally expensive to resolve. Instead, the application of intensity density ratios to this invention results in real and measurable computational efficiencies with tolerances toward uncalibrated reference images. Although, image normalization is not precluded in the invention.

As a supplemental metric to the image intensity density, the magnitude positioning of the normal and anomalous intensity ranges to each other will be categorized as either 'over' (anomaly is more dense than normal tissue), or 'under' (anomaly is less dense than normal tissue). Other categories may also be provided depending on, for example, the images.

As an additional or alternative supplemental metric to the image intensity density, the size (area and/or volume) of the anomaly may also be computed and stored in the database along with the approximate shape of the anomaly. Analytical information will be manually entered for each historical anomaly, or obtained automatically from a file associated with the image. The invention may include, but is not limited to, one or more of the following characteristics: age of the subject, sex of the subject, classification of the anomaly, diagnosis of the anomaly, prescribed treatment, subsequent outcome, and time to resolution.

The metrics described above are preferred measurements for this invention, but the invention is not restricted to only these measurements. Other statistical measurements as known to those skilled in the art, whether existing or conceived of in the future, may be incorporated into this step.

Such measurements are projected to be more beneficial when used in conjunction with the invention's dynamically sized, moving container innovation described below. For instance, in other embodiments of the invention, skewness (the measurement of the overall intensity shift of a group of samples) could serve as an additional metric to detect when the moving container is translating between regions of different intensity and denoting a possible anomalous or structure boundary. In yet another embodiment of the invention, kurtosis (the measurement of the peakedness of the intensity of the group of samples) could serve as an additional metric used to detect when the moving container is in an area of different image intensity consistency when compared to the previous container location. Kurtosis may be used in addition to or instead of skewness. The inclusion of these and other measurements serve only to improve the invention's ability to discover subtle and exceptional anomalies and do not negate the uniqueness of the invention's overall sequence.

The aforementioned metrics and analytical information will reside in a database 10 created, used and managed in accordance with the teachings of the invention as described herein. In preferred embodiments, the database 10 is organized into categories of major body regions as listed in FIG. 1. FIG. 1 shows, as an example only, a columnar format for the database 10, and without metrics associated with the secondary components (which are illustrated in FIG. 2). One skilled in the art would appreciate that this columnar structure is for explanation of the database only and the database can be organized in any known manner. Thus, there are no implied restrictions on the database organization because there are variations that may be more efficient under certain conditions as one skilled in the art would recognize while still in keeping with the concept of the invention.

In a first column of the database shown in FIG. 1, primary categories of anatomical parts are listed, e.g., head, torso and extremities (limbs). In a second column of the database, one or more components in each primary category are listed, e.g., brain, nasal, optic system, and otic system for the head, organs, muscle, skeletal structure and circulatory system for the torso and arms and legs for the extremities. In a third column of the database, secondary components of each of the components in the second column are listed, e.g., frontal lobe, parietal lobe and temporal lobe for the brain.

Once the database has been created or defined, it will be utilized in the analysis of new medical images. A software algorithm, embodied as code on computer readable medium that is executed by a processor of a computer, will receive as input, an electronic image (picture) of a component of the body containing position-relative intensity information (grayscale values). Preferred embodiments of the invention will recognize the majority of industry-standard lossless file formats such as, but not limited to, BMP, DICOM, PNG, and RAW, but there is no implied restriction as to the format of the data.

If the image contains a structure and density that is known to be generally consistent throughout, such as breast tissue, the image may be directly processed by the software algorithm.

If the image contains a structure and density that is known to be nonhomogeneous or inconsistent, such as a human head or torso, the image is preferably segmented by external means, such as that described above using a pen tablet or computer mouse, or with an automated means, so that only a structure consistent with the region being analyzed and the analogous entries within the database, is presented to the algorithm. This enables an effective analysis of the region to be analyzed relative to data contained in the database.

Utilizing the database, the invention will reference predetermined metrics of anomalous structures for each segment of the human anatomy, to compare against calculated metrics derived from the current image under test. The object of the comparison is that if a metric match is found with an anomalous object in the database, the probability of the test image having the same diagnosis, i.e., the anomaly, is very high.

Referring in this regard to FIG. 2, FIG. 2 shows a subset of database organization with metric entries for two secondary components, the parietal lobe and the temporal lobe as examples. For the parietal lobe, there are four entries, and analytical information for each entry. The analytical information includes age, sex, area of anomaly, shape of anomaly, additional medical testing performed with test results, diagnosis, prognosis, treatment, outcome and time to resolution. All of these may be provided, or only a portion, e.g., if some are not known. Metrics are associated with the entry in the last column, including those discussed above, such as intensity range ratio, passing threshold for intensity range ratio comparison, intensity range positioning, intensity density ratio, passing threshold for intensity density ratio comparison and intensity density positioning. For each entry and for each secondary component, information is provided to complete the database.

The database 10 is dynamic and managed in the sense that the results from each test will be incorporated back into the database 10 for utilization by future applications. The thoroughness and accuracy of the algorithm will improve as it examines more and more images with varying metrics. It is an object of the invention to present possible anomalies that are difficult to detect by historical methods and thus decrease the occurrences of 'false positive' diagnoses. The operator of the invention, preferably a radiologist, is responsible for the examination of the algorithm's findings and the final determination of the diagnosis.

Analysis of the test image will produce the same calculations that were described above for the images being datamined with the exception that the test image may or may not have potential anomalies delineated by the operator. If no delineations are available, the entire test image will be examined from the standpoint of whether it possesses similar metrics to the anomalous entries in the database. The operator will identify to the algorithm which bodily category the test image belongs to, although this identification might also be performed automatically by a software application, and sequentially, the algorithm will access the metrics of each database entry in that category.

Independent of the formation of the database 10 as described above, the invention also relates to a technique using a "moving container". This technique may be used independent of the database 10 or in combination therewith.

In this technique, the invention may be designed to retrieve the approximate size and shape of the database entry's anomaly and construct a two dimensional 'virtual' container of the same dimensions. The terminology 'virtual' means that the container is a software storage construct and not an actual container.

A system and method for implementing grid-based image segmentation is known. However, a problem exists where the rigidity of a fixed grid approach allows feature anomalies to be split between grid lines, thus making anomaly identification fragmented or overlooked.

In a preferred embodiment, and in contrast to the known image segmentation methods and systems, the present invention implements a pixel-incremented algorithmic search using sequentially adjacent two-dimensional subsets of the image data, known henceforth as a 'moving container', comparing the measured metrics of each subset to the expected metric values from the database, in effect looking for intensity value groupings that are not homogenous with surrounding values. This analysis is generally based on a subset of the medical image data obtained by a medical imaging device, wherein multiple and different subsets of the medical image data are analysis independently or subjected to the same analysis.

Another important feature is that the shape and size of the moving container may be variable and determined based on the historic anomalous shapes and sizes as retrieved from the database. For example, a tumor recorded in the database may have had an oval shape with a larger cross section in the X axis. The invention would calculate a two dimensional container with the approximate dimensions for the following sequence.

The algorithm will electronically place the container over the test image at an initial location and incrementally move it to another location by the smallest unit possible (one pixel or one line) while calculating the intensity density ratio metric at each location. If the intensity density ratio is within a predetermined percentage, e.g., five percent in a preferred embodiment, of the intensity density ratio recorded for the database image, the algorithm will then calculate the metric for the intensity range ratio for the present location of the container.

In order to reduce manual inspection of parts of the test image, a routine is provided to perform preliminary analysis. This routine is exemplifying only and other techniques to analyze locations of images to determine which are worthwhile to manually inspect, and which are not, are also contemplated to be within the scope and spirit of the invention. In the exemplifying embodiment, if the intensity range ratio is within a predetermined percentage, five percent in a preferred embodiment, of the intensity range ratio recorded for the database image, the current location is determined to be worthy of manual inspection.

It is obvious that the necessary processing time for analyzing a high resolution image using repetitive minimal increments will be very high, and in the context of performing this operation multiple times, will potentially require significant periods of time to perform the desired analysis. In a preferred embodiment of the invention, a copy of the original high resolution image will be made and its resolution will be reduced by a numerical factor in order to reduce the quantity of analysis of redundant insignificant data. The factor may be chosen on a sliding scale so as to not prevent detection of an anomaly by removing too much image (data) detail. The calculation of the factor is typically based upon the original resolution of the image (more reduction if the image is very detailed) and the estimated size of the region of interest (less reduction if the region of interest is small). Ideally, the resolution reduction will be a factor of 3, which produces a data (and processing time) reduction of 9 times (three squared). In the sequential operation of the method, once an area of interest has been identified (the measured metrics correlate to metrics stored in the database), the method will apply the same area of interest (the container) to the corresponding location in the original full resolution image in order to accomplish the most accurate assessment possible. This operation is analogous to 'zooming in' to an image with a camera lens. One benefit of such a method is a substantial improvement in processing time while producing the same analytical results.

The percentage thresholds described above are anticipated to vary from image to image in the database due to inconsistency in the images recorded by the medical instruments. The thresholds may be predetermined or based on analysis conditions. The invention acknowledges this inconsistency by allowing the percentage threshold, or other type or form of threshold other than expressed in percentage form, to be stored with or in association with each image in the database. In one envisioned embodiment, larger tolerances would be assigned to images with poor exposures (images with compressed or skewed dynamic range) while smaller tolerances would be assigned to images with correct exposures. It should be obvious to one skilled in the art to which this invention pertains, that despite having determined that the test image has a potentially anomalous area, it is highly improbable that two anomalies having similar characteristics will also have an identical shape and size. The invention acknowledges this improbability and defines the next step to refine the outline of the anomaly. The algorithm will retain the shape of the virtual container as retrieved from the database or constructed from data retrieved from the database, but reduce the size of it by a factor of for example, 0.5 (step 30 of FIG. 3 described below). As before, the modified container will be incrementally scanned across the test image and the intensity density ratio and intensity range ratio will be calculated or otherwise determined (step 34 of FIG. 3 described below).

When results match within the threshold, an entry for each point located within the current container will be counted on a results tracking map which contains individual counts for each point in the entire image (steps 36 and 38 of FIG. 3 described below). As the container is moved over the test image to a plurality of different positions or locations, other container locations will verify positive due to the reduced size of the container and redundant points will be counted and recorded on the results tracking map. Duplicate points verified as positive when the container is in different positions will increment the count of that point on the tracking map.

When the container movement sequence is complete, i.e., the container has been scanned over the entire image and there are no more positions (step 40 of FIG. 3 described below), by definition, the tracking map will show a weighted representation of where the intensity density ratio and intensity range ratio matched the database metrics.

Next, the invention will calculate an artificially colored contour map, as known to one skilled in the art to which this invention pertains, from the tracking map, preferably drawing concentric lines around points with equivalent counts (points that were redundantly verified), and then overlay these contour lines on the original test image for the visual presentation to test operator (steps 44 and 46 of FIG. 3 described below). The contour lines will delineate the area of the test image that was closely matched with image metrics from an entry in the database 10. In the visual presentation to the operator, on a computer monitor or other such medium, the information recorded with the database anomaly will be displayed for reference purposes (step 48 of FIG. 3 described below).

In the event that the chosen entry from the database shows no correlation to the test image (i.e., the metrics are outside of the specified tolerance), the algorithm proceeds to the next database entry and repeats the operation. If all appropriate database entries have been processed, it is the conclusion of the algorithm that the test image shows no similarity to historical anomalous images and must therefore be (manually) analyzed by the test operator relative to itself and the patient's history.

Figure 3:
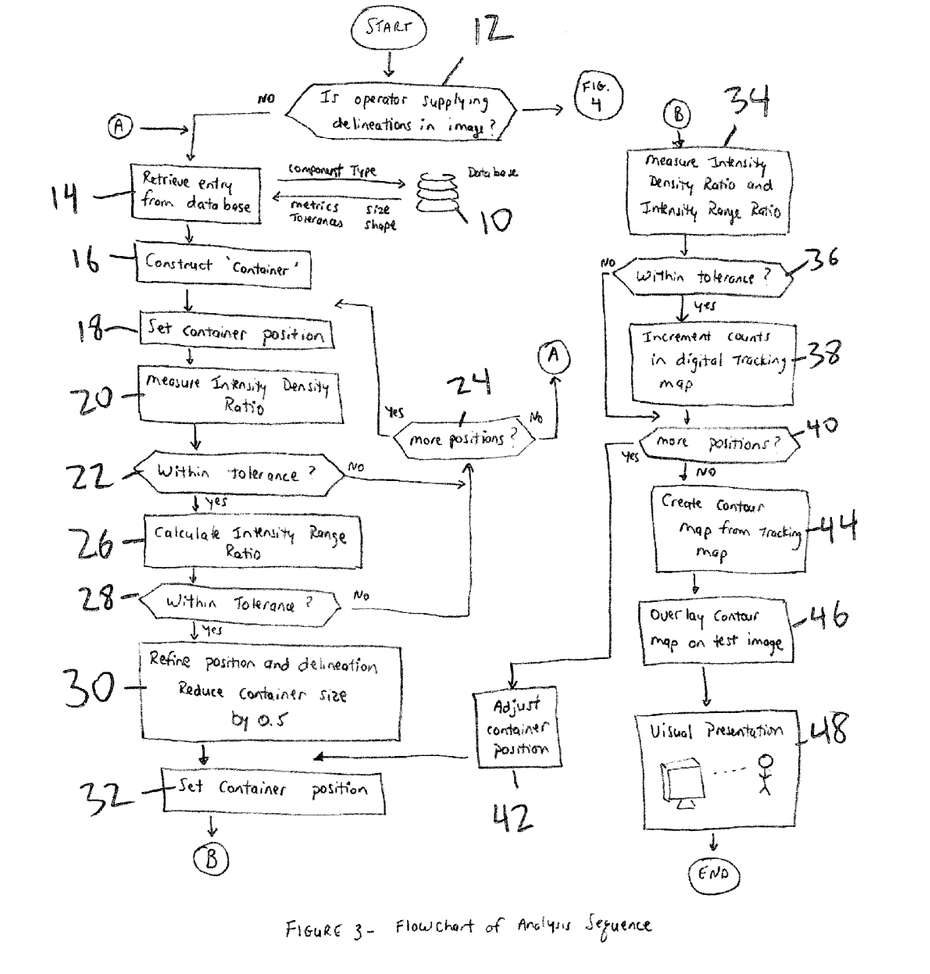
FIG. 3 shows a sample flow chart of the sequential steps of the algorithm (test image with no delineations)

The foregoing steps are schematically depicted in FIG. 3. The first step 12 is to determine whether an operator is supplying delineations in an image. If so, the process proceeds to FIG. 4, discussed below. If not, then an entry is retrieved from the database 10 in step 14. This retrieval may be performed by providing the component type of the database 10 and obtaining from the database 10, the metrics, tolerances, size and shape of the anomaly (as depicted). From the retrieved entry, a container is then constructed in step 16, an initial position of the container is set in step 18 and the intensity density ratio is measured in step 20. A determination is made in step 22 whether the measured intensity density ratio is within a tolerance, e.g., a predetermined tolerance. If not, a determination is made as to whether there are more positions for the container in step 24 and if so, the container position is moved and the process proceeds to step 18. If there are no more positions, then the process proceeds to step 14 and another entry is retrieved from the database 10.

If the measured intensity density ratio is within the tolerance as determined in step 22, then the intensity range ratio is calculated in step 26 and a determination is made in step 28 whether the calculated intensity range ratio is within a tolerance, e.g., a predetermined tolerance. If not, a determination is made as to whether there are more positions for the container in step 24 and if so, the container position is moved and the process proceeds to step 18. If there are no more positions, then the process proceeds to step 14 and another entry is retrieved from the database 10.

On the other hand, if the calculated intensity range ratio is within a tolerance as determined in step 28, the position is refined and delineated, and the container size is reduced by, for example, 0.5, in step 30. The container position is then set in step 32 and the process proceeds to step 34

In step 34, the intensity density ratio is measured along with the intensity range ratio. A determination is made in step 36 whether the measured intensity density ratio and intensity range ratio are within tolerances, e.g., predetermined tolerances. If so, the count in a digital tracking map is incremented in step 38 and then a determination is made in step 40 whether there are more positions. If the measured intensity density ratio and intensity range ratio are not within tolerances, then the process proceeds directly to step 40. When there are more positions as determined in step 40, the container position is adjusted in step 42 and the process proceeds to set the container position in step 32 and continues from there as described above.

On the other hand, when it is determined in step 40 that there are no more positions, a contour map is created from the digital tracking map in step 44 and in step 46, the contour map is overlaid on the test image. A visual presentation is made in step 48 on a display, computer monitor or other display device that is coupled to the processor that is performing the steps described above.

In a different embodiment of the invention, the database would be organized in different ways for the purpose of efficiency and to maximize the processing speed of the algorithm as known to those skilled in the art to which the invention pertains. For instance, the entries in the database 10 could be arranged by frequency of occurrence. In other words, the image under test would be tested first for the anomalies that occur most often and that data would be given priority when retrieving entries from the database 10. Furthermore, the database 10 could be arranged in a method which links one or more specific anomalies together if there are reported instances of multiple anomalies occurring together. Such a feature would be utilized to recommend diagnostic testing of other regions if there is a statistical probability that another anomaly might be present.

In the event that the operator supplied a delineated region of interest in the test image to the invention, a slightly different sequence is followed (schematically outlined in FIG. 4, described below). The container will be assigned to be the region of the delineation but reduced in size by five percent, in preferred embodiments, and the metrics will be measured or otherwise determined within that region (steps 50, 52, 54 in FIG. 4). If the intensity density ratio is within the percentage of the intensity density ratio defined in the database, the algorithm will then calculate or otherwise determine the metric for the intensity range ratio for the container (steps 56 and 58 in FIG. 4). If the intensity range ratio is within the percentage of the intensity range ratio recorded in the database, the delineated location is determined to be worthy of manual inspection.

It should be obvious to one skilled in the art, that a visually determined delineation is likely to have an inaccurate border. The invention acknowledges this probability and defines the next step to refine the delineated outline of the anomaly (step 62 in FIG. 4). The algorithm will retain the shape of the delineation as specified by the operator, but reduce the size of it by a factor of 0.5 or another factor determined by the operator or based on, for example, characteristics of the image.

Figure 4:
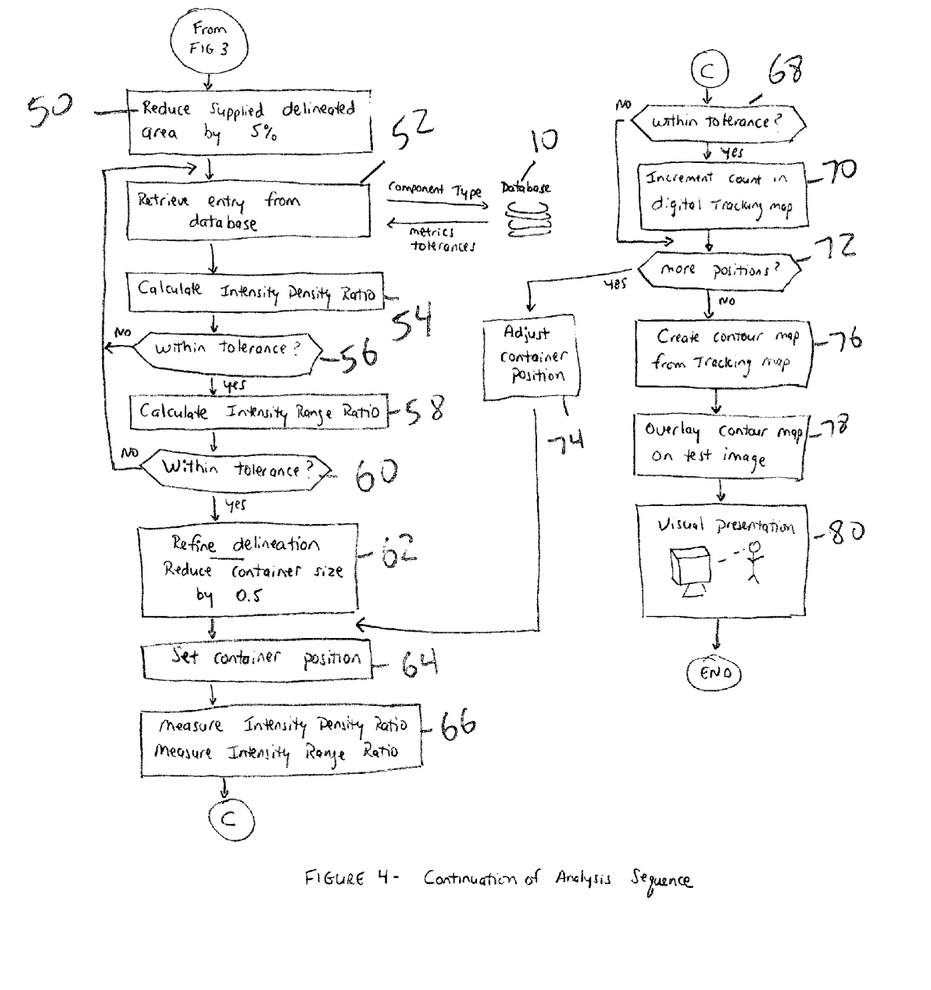
FIG. 4 shows a sample flow chart of the sequential steps of the algorithm (test image with delineations)

The modified container will be incrementally scanned in the local neighborhood of the delineated anomaly (i.e., within positions that are within for example, about 10 percent in preferred embodiments) and the intensity density ratio and intensity range density will be calculated or otherwise determined (step 66 in FIG. 4). When the results match within the threshold specified in the database, an entry will be counted and tracked on a results tracking map for each point located within the current container (steps 68, 70 in FIG. 4). As the container is moved over the test image to different positions or locations, other container locations will verify positive due to the reduced size of the container and redundant points will be recorded on the tracking map. Redundant points verified as positive when the container is in different positions will increment the count of that position on the tracking map.

When the container movement sequence is complete, i.e., there are no more positions of the container, the tracking map will show a weighted representation of where the intensity density ratio and intensity range ratio matched the database metrics. The invention will calculate an artificially colored contour map, as known to one skilled in the arts, from information stored in the tracking map, drawing concentric lines around equivalent counts (points that were redundantly verified), and then overlay these contour lines on the original test image for the visual presentation to test operator (steps 76, 78 in FIG. 4). The contour lines will delineate the area of the test image that was closely matched with an image metrics from an entry in the database.

Referring more specifically to FIG. 4, when the operator is determined to be supplying delineations in the image in step 12, the supplied delineated area is reduced by a set percentage, e.g., 5%, in step 50. Then an entry is retrieved from the database 10 in step 52. This retrieval may be performed by providing the component type of the database 10 and obtaining from the database 10, the metrics, tolerances, etc. of the anomaly (as depicted). From the retrieved entry, the intensity density ratio is calculated or otherwise determined in step 54. A determination is made in step 56 whether the calculated intensity density ratio is within a tolerance, e.g., a predetermined tolerance. If not, another entry is retrieved from the database 10 in step 52.

If the measured intensity density ratio is within the tolerance as determined in step 56, then the intensity range ratio is calculated or otherwise determined in step 58 and a determination is made in step 60 whether the calculated intensity range ratio is within a tolerance, e.g., a predetermined tolerance. If not, another entry is retrieved from the database 10 in step 52.

On the other hand, if the calculated intensity range ratio is within a tolerance as determined in step 60, the delineation is refined, and the container size is reduced by, for example, 0.5, in step 62. The container position is then set in step 64 and the intensity density ratio is measured along with the intensity range ratio in step 66. A determination is made in step 68 whether the measured intensity density ratio and intensity range ratio are within tolerances, e.g., predetermined tolerances. If so, the count in a digital tracking map is incremented in step 70 and then a determination is made in step 72 whether there are more positions. If the measured intensity density ratio and intensity range ratio are not within tolerances, then the process proceeds directly to step 72. When there are more positions as determined in step 72, the container position is adjusted in step 74 and the process proceeds to set the container position in step 64 and continues from there as described above.

On the other hand, when it is determined in step 72 that there are no more positions, a contour map is created from the digital tracking map in step 76 and in step 78, the contour map is overlaid on the test image. A visual presentation is made in step 80 on a display, computer monitor or other display device that is coupled to the processor that is performing the steps described above.

In the event that the chosen entry from the database shows no correlation to the test image (i.e., the metrics are outside of the specified tolerance), the algorithm proceeds to the next database entry and repeats the operation. If all appropriate database entries have been processed, it is the conclusion of the algorithm that there is no region within the test image that shows similarity to historical anomalous images and must therefore be (manually) analyzed by the test operator relative to itself and the patient's history.

In the event that a potential anomaly has been identified, it is an object of the invention to present the information visually on, but not limited to, a display monitor. The display may consist of the original medical image with an artificially colored contour map showing the anomaly in the proper location. Other information will be optionally displayed on the monitor, such as the context information accompanying the final shape and size of the container that was utilized from the database. Such context information may also include, but is not limited to, anomaly diagnosis/prognosis, diagnostic tests performed and their reports, treatment, outcome, and age and gender.

Of great importance to the invention is the historical record of diagnostic tests, their findings and subsequent diagnosis. In a traditional sequence of discovery, a physician would order a series of noninvasive diagnostic procedures, such as imaging scanning, followed by invasive diagnostic procedures, such as biopsy testing, in order to form a diagnosis. The biopsy tests would report its finding including possibly whether the suspect anomaly was malignant or nonmalignant and in effect, prove or disprove the findings of the initial diagnostic imaging where the anomaly was first suspected. By reverse connecting these diagnostic findings stored in the database (i.e., the malignant/nonmalignant mass that was detected through a biopsy test confirms that initial medical image presents/does not present an anomaly as specifically represented in the accompanying metrics), the detection of the anomaly can now occur during metric analysis eliminating the need to incur the extraordinary cost and delay of additional medical test procedures. This efficiency in procedure provides the real and tangible benefit of a quicker and more accurate diagnosis leading to lower treatment expenses and optimizing the chances for a successful recovery by finding the anomaly at the earliest possible stage, or at least hopefully at an early stage of growth.

Preferred embodiments of the invention will also have the ability to incorporate the final results determined by the algorithm back into the database 10. If the operator of the invention confirms that the object presented is indeed an anomaly, the operator is queried to provide the context information about the anomaly and a new record is created inside the database 10 with the information. The information recorded consists of, but is not limited to, the size and shape of the container used in the detection, anomaly diagnosis/prognosis, treatment, outcome, and age and gender (see FIGS. 1 and 2).

Figure 5:
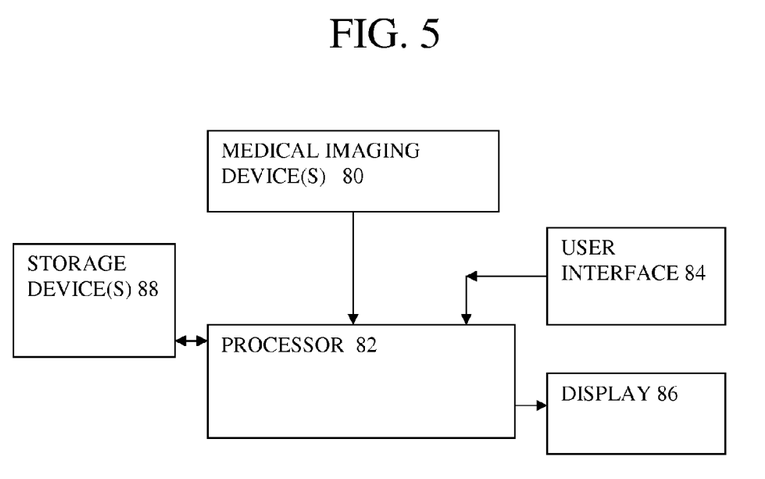
FIG. 5 is a schematic showing a system that performs the method in accordance with the invention.

Referring now to FIG. 5, a system implementing any of the methods described above includes a processor 82, to which one or more medical imaging devices 80 may be coupled. This coupling may be, for example, through wired means, wireless means, an intranet or the Internet. Also, the medical imaging devices 80 may operate and create data that is loaded onto a memory component and then this memory component coupled to the processor 82. The medical imaging devices 80 may be considered part of the invention or not, i.e., when the invention is considered only the processor 82 and its functionality. A user interface 84, representing either a single user interface or a plurality of user interfaces, is connected to the processor 82 to enable the user to provide commands thereto, and a display or display device 86 is also coupled to the processor 82 to present results of the testing to the user. One or more memory or data storage devices 88 are also coupled to the processor 82 and include, for example, the database 10.

With the foregoing structure, a basic system for analyzing a medical image in accordance with the invention includes a database 10, 88 containing sets of a plurality of specific metrics derived from both anomalies and non-anomalous regions in a plurality of historical medical images, at least one medical imaging device 80 that obtains a medical image under test for analysis and can optionally prepare the obtained image for subsequent processing, and a processor 82 coupled to the database 10, 88 and the medical imaging device 80. The processor 82 is configured to determine the plurality of specific metrics from the medical image under test obtained by each medical imaging device 82 (processing it into a workable format if necessary and not already undertaken by the medical imaging device 80), and is then configured to compare the plurality of metrics from the medical image under test to the sets of the plurality of metrics from the database 10, 88 to determine a degree of similarity therebetween (as described above). The processor 82 is also configured to create a contour map based on the determined degree of similarity. Then, the display device 86 coupled to the processor 82 is directed by the processor 82 to display the created contour map on the medical image under test. With the user interface(s) 84, the user can delineate regions of the medical image under test while viewing the medical image under test on the display device 86. The delineation is, in a processing technique known to those skilled in the art, processed by the processor 82 which responds by determining the plurality of specific metrics for each delineated region of the medical image under test and then comparing the plurality of metrics from each delineated region of the medical image under test to the sets of the plurality of metrics from the database 10, 88 to determine a degree of similarity therebetween. The same physical components are also capable of executing the steps of method described above and explained with reference to FIGS. 3 and 4, while the database may have the properties described above and explained with reference to FIGS. 1 and 2.

Several computer programs resident on transitory or non-transitory computer-readable media may be used in the invention and their function and non-limiting location are mentioned above. In the context of this document, computer-readable media or medium could be any non-transitory means that can contain, store, communicate, propagate or transmit a program for use by or in connection with the method, system, apparatus or device. The computer-readable medium can be, but is not limited to (not an exhaustive list), electronic, magnetic, optical, electromagnetic, infrared, or semi-conductor propagation medium. The medium can also be (not an exhaustive list) an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM). The medium can also be paper or other suitable medium upon which a program is printed, as the program can be electronically captured, via for example, optical scanning of the paper or other medium, then compiled, interpreted, or otherwise processed in a suitable manner, if necessary, and then stored in a computer memory. Also, a computer program or data may be transferred to another computer-readable medium by any suitable process such as by scanning the computer-readable medium.

One computer program, embodied in computer readable media and executed by a processor coupled to the media, is configured to cause the processor to interact with a medical imaging device to obtain a medical image under test to be analyzed, access a database containing sets of a plurality of specific metrics derived from both anomalies and non-anomalous regions in a plurality of historical medical images to enable retrieval of sets of the plurality of specific metrics, direct that same processor or a different processor to determine the plurality of specific metrics from the obtained medical image under test, direct a processor to compare the plurality of metrics from the medical image under test to each retrieved set of the plurality of specific metrics from the database to determine a degree of similarity therebetween, direct a processor to create a contour map based on the determined degree of similarity, and direct a display device to display the created contour map on the medical image under test. The processing functions may be performed by a singular processor or multiple processors.

Figure 6:
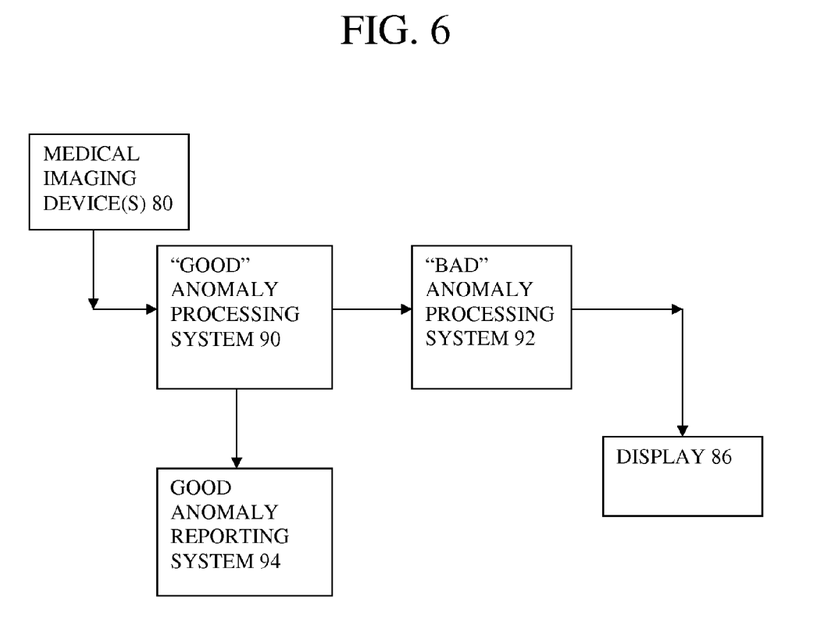
FIG. 6 is a schematic drawing of another system that incorporates the method in accordance with the invention.

Referring now to FIG. 6, another embodiment of the invention, that utilizes one or more of the techniques described above, provides for a highly efficient determination of the presence of an anomaly that requires manual attention. In this embodiment, a database of "good" or normal anomalies is first accessed in a preprocessing step, which is intended to eliminate some or all of the anomalies detected in the medical image under test from further processing in the aforementioned sequence of determining the presence of a "bad" or abnormal anomaly on the basis that these "good" anomalies are not problematic. The premise of "good anomalies" is a preferred and, at times, necessary consideration because abnormalities exist in living tissue, which despite being uncommon (i.e., not present in every living form), do not likely represent a harmful, diagnosable condition and thus, should be excluded from further consideration. At a minimum, the good anomalies should be temporarily put aside to focus on the analysis of "bad" or abnormal anomalies. For example, those skilled in the art will readily recognize that the presence of certain physicalities, including but not limited to, small air pockets and calcium deposits, which exhibit inconsistent occurrence and placement, are not typically cause for concern or treatment.

Thus, from the medical imaging device 80 that obtains the medical image under test, a good anomaly processing system 90 is utilized to compare a plurality of specific metrics derived from delineated regions of the medical image under test to the same plurality of metrics associated with good anomalies. This comparison may be performed by comparing the metric or metrics of a delineated region of the medical image under test to the same metric or metrics of a delineated region of a historical medical image representing a good anomaly, i.e., an anomaly that is not diseased, that is not infected, that is not abnormal, that is not operating incorrectly, etc. The comparison may involve determining a degree of similarity between the plurality of specific metrics from the medical image under test obtained by the medical imaging device and the sets of the plurality of metrics from one or more accessed databases of "good" anomalies. If the degree of similarity is equal to or above a threshold, indicating a high likelihood or probability of the anomaly being a "good" anomaly, the anomaly may be removed from further analysis. On the other hand, if the degree of similarity is below this threshold, indicating it does not appear similar to any of the good anomalies, the bad anomaly processing system 92 is accessed, described below.

Each database of good anomalies may be derived by obtaining medical images of healthy body components, deriving the metrics therefrom and then storing the metrics in a database, such as in the manner shown in FIGS. 1 and 2.

The invention also considers the size and location of "good" anomalies. If the manifestation of the "good" anomaly exceeds a predetermined size (area), and/or occurs in a predetermined region where the "good" anomaly should not exist, the determination of "good anomaly" will be modified to "bad anomaly" and the process will continue with the anomaly outline defining methods prescribed in the bad anomaly processing system 92 and ultimately, potential final presentation to the test operator. Thus, the "good anomaly" database should contain, as part of its metrics, a limiting threshold size (area) for the anomaly, above which the anomaly is no longer considered "good". In addition, the "good anomaly" database should contain, as part of its metrics, an allowable location metric denoting where the anomaly may occur and still considered to be "good". Anomalies occurring outside of this region will no longer be considered "good". The "good anomaly" database is not limiting in the types of metrics that it may consider in the comparison process and thus may include other metrics as known to those skilled in the arts.

By positioning a good anomaly processing system 90 as the first stage in the processing of the medical image under test obtained by the medical imaging device 80, all anomalies that do not require attention, i.e., are not problematic and represent healthy body components, or that do not require immediate attention, can be removed from further processing. In an ideal case, all anomalies will be determined to be good anomalies, which means that the medical image does not indicate the presence of a diseased, abnormal or unhealthy body component. This can be reported on the good anomaly reporting system 94, i.e., on a display or other notification device provided to the image or test taker. The good anomaly reporting system 94 may be on the same unit as the good anomaly processing system 90 and optionally the medical imaging device 80. It may also be a wireless device available to the patient's physician or treatment coordinator.

However, in a non-ideal case, there will be at least one "bad" anomaly that is not screened out by the good anomaly processing system 90 and is input to the bad anomaly processing system 92. The bad anomaly processing system 92 operates using the techniques described above to analyze the specific delineated regions of the medical image under test that have been found not to be "good" and compares these regions to metrics of historical medical images that contain bad anomalies, e.g., body components that are diseased, abnormal, infected, etc. After analyzing the bad anomalies, an analysis is provided to the display device 86. This analysis may be in the form of a contour map created based on the determined degree of similarity between the plurality of metrics from the medical image under test and the sets of the plurality of metrics from one or more databases of "bad" anomalies.

This embodiment therefore has a two-stage processing system wherein a filtering of sorts is performed to optimize use of the bad anomaly database. The amount of delineated regions of the medical image under test being analyzed by the bad anomaly processing system 92 is almost always fewer than the total number of delineated regions, since at least some portion of the medical image under test is highly likely to be normal, i.e., contain only "good" anomalies. In other words, the benefit of utilizing a "good anomaly" preprocessing stage via the good anomaly processing system 90 is that it will produce a much higher processing efficiency because the "good anomaly" database will almost always be smaller than the "bad anomaly" database, thus eliminating a large number of metric comparisons with "bad anomaly" metrics, the results of which would all be negative anyhow. Another important benefit is that anomalies (which are "good") will not be erroneously added to the "bad anomaly" database after no match has been identified in the comparison sequence.

Instead of having a good anomaly database and a separate bad anomaly database, it is possible to have different databases that are accessed sequentially with an overall view toward optimizing use of the last accessed database. The first database accessed may be one with common anomalies (such as the "good" anomalies described above) or anomalies that do not require immediate attention, while the second database accessed may be one with anomalies that require immediate attention. In this case, pre-processing removes anomalies that do not necessitate immediate action and reduces the data used in the comparison performed accessing the second database so that anomalies requiring immediate attention may be identified quicker and more expeditiously.

In keeping with the invention's spirit of efficiency, yet another embodiment of the invention combines one or more of the techniques listed above with the physical medical imaging device to form a single homogeneous instrument. The instrument will embody all of the elements known to produce the image scan using known and unknown technologies, as well as the processing unit, anomaly database(s) and prescribed analysis sequence enabling the instrument operator to produce an automatic analysis on-site. This single homogenous unit may be portable or installed on a single wheeled cart or other wheeled unit for easy access in a physician's office, hospital or other medical imaging location. The manner in which the medical imaging device that obtains images for analysis and the processor that analyzes the images relative to the database may be physically combined into a single homogenous unit would be evident to those skilled in the art in view of the disclosure herein, for example, mounting on a common structure and providing an appropriate coupling therebetween with proper communications protocol.

As used herein, the term "highlight" will generally mean to mark with an easily recognizable indication, usually a color that differs from other colors in the background of the image or other signal being highlighted. However, the term also encompasses any other indication, designation or demarcation of an area on an image or signal using one or more of color, lines, shapes, forms and/or text.

With the foregoing structure and operational steps, new intelligent and efficient methods, systems, arrangements, apparatus and computer programs, including use of software algorithms, are provided to analyze medical imagery for all known possible anomalies.

Further, methods, systems, arrangements, apparatus and computer programs are disclosed that benefit from the vast number of existing medical images (that are kept as historical records and will serve no future use) by combining the historical data that was provided by the original analysis of these images with the knowledge of the subsequent outcome. Even Even further, methods, systems, arrangements, apparatus and computer programs are disclosed that create and manage a database containing the information derived from the examination, analysis and/or categorization of these existing medical images.

Still further, methods, systems, arrangements, apparatus and computer programs are disclosed that utilize a database containing historical information in the analysis of new medical images by enabling unique comparison methods using specific metrics to determine the existence of anomalies (cancers, tumors, growths, diseases presenting abnormal internal structures, and other) in unanalyzed medical images.

Furthermore, methods, systems, arrangements, apparatus and computer programs are disclosed that utilize the historical data in the database to guide the diagnosis of anomalous structures and to recommend/not recommend further diagnostic procedures.

Also, methods, systems, arrangements, apparatus and computer programs are provided that enable addition of entries to a database of historical anomalies on the occasion that a newly diagnosed anomaly was not detected during the search sequence and also was not present in the anomaly database.

Having thus described a few particular embodiments of the invention, various alterations, modifications, and improvements will readily occur to those skilled in the art. For instance, the invention can be adapted to other methods of moving the container through the image or the altering the types of historical metrics available in the database. Such alterations, modifications and improvements as are made obvious by this disclosure are intended to be part of this description though not expressly stated herein, and are intended to be within the spirit and scope of the invention. Accordingly, the foregoing description is by way of example only, and is not limiting. The invention is limited only as defined in the claims and equivalents thereto.

What is claimed is:

1. A method for analyzing a medical image, comprising:
   retrieving, from a database, at least one set of a plurality of specific metrics from a plurality of sets of metrics stored in the database, each of the sets of metrics stored in the database being derived from an anomaly or a non-anomalous region in an associated one of a plurality of historical medical images such that at least one set is derived from an anomaly of an associated historical medical image and at least one set is derived from a non-anomalous region of an associated historical medical image, each of the metrics in each set of metrics being a different measurement of the associated historical medical image;

obtaining a medical image under test by means of a medical imaging device;

determining, using a processor, the plurality of specific metrics from the obtained medical image under test, each of the metrics being a different measurement of the obtained medical image;

comparing, using a processor, the plurality of determined metrics from the medical image under test to the retrieved at least one set of the plurality of metrics from the database to determine a degree of similarity therebetween, the comparison step comprising comparing each of the determined metrics from the medical image under test to a respective one of the metrics of the retrieved at least one set of the plurality of metrics from the database;

creating, using a processor, a contour map based on the determined degree of similarity between the plurality of determined metrics from the medical image under test and the retrieved at least one set of the plurality of metrics from the database; and displaying the created contour map on the medical image under test on a display.

2. The method of claim 1, further comprising storing the specific metrics derived from anomalies and non-anomalous regions in historical medical images in the database arranged by body categories, components of the category, and secondary components of the category.

3. The method of claim 1, further comprising storing additional information related to the historical medical images in the database that include anomalies, including for each such medical image, patient age, patient sex, area of anomaly, shape of anomaly, diagnostic tests performed and their reports, diagnosis/prognosis, treatment, outcome, time to resolution, and actual medical image.

4. The method of claim 3, further comprising:
forming the database from the historical medical images; and
when forming the database, reducing an overall size of the historical medical images using a processor by delineating an outer boundary of any anomaly in each historical medical image, then enlarging the delineated outer boundary to provide an enlarged contour of the diagnosed anomaly, and using the enlarged contour of the diagnosed anomaly in metric calculations to be saved in the database.

5. The method of claim 1, further comprising organizing the database to include a cross reference indication when one anomaly in a historical medical image in the database occurs simultaneously with one or more other anomalies in one or more other historical medical images in the database, the cross reference indication inferring a relationship between the anomalies in the two or more historical medical images when any of the linked anomalies is retrieved.

6. The method of claim 1, wherein the specific metrics consists of one or more of the following:
an intensity range of a region of the anomaly,
an intensity range of the non-anomalous region,
a ratio between the intensity range of the anomaly and the intensity range of the non-anomalous region,
a variance of the anomaly region,
a variance of the non-anomalous region, and
a ratio between the between the variance of the anomaly region and the variance of the non-anomalous region.

7. The method of claim 1, further comprising enabling a user to vary, using a user interface, the metrics determined for the medical image under test.

8. The method of claim 1, further comprising calculating, using a processor, the metrics from the historical medical image with manual delineations of the anomalies.

9. The method of claim 1, further comprising enabling manual delineations of the medical image under test using at least one user interface.

10. The method of claim 1, wherein the medical image under test does not have manual delineations, further comprising:
retrieving at least one analogous entry from the historical medical image database related to the medical image under test; and
configuring a subset of the medical image under test from which the plurality of specific metrics is determined as a virtual container of size and shape derived from the retrieved at least one analogous entry from the historical medical image database such that the specific metrics are determined based only on that portion of the medical image under test in the virtual container.

11. The method of claim 10, further comprising moving the virtual container incrementally across the medical image under test to different positions, the plurality of specific metrics being determined at each of a plurality of positions to which the virtual container is moved.

12. The method of claim 11, further comprising:
moving the virtual container incrementally across a reduced resolution of the original medical image under test, when resolution of the original image exceeds a programmable threshold; and
comparing the metrics from the medical image under test to the metrics stored for each of a plurality of analogous entries retrieved from the historical medical image database until a successful condition is determined by using a pass/fail threshold metric stored in the database as the criteria, the successful condition being present when one of the analogous entries retrieved from the historical medical image database passes the threshold metric.

13. The method of claim 12, further comprising:
applying an identical virtual container to an equivalent location within the original high resolution image under test; and
repeating the aforementioned analysis using the original high resolution image.

14. The method of claim 11, further comprising comparing the metrics from the medical image under test to the metrics stored for each of a plurality of analogous entries retrieved from the historical medical image database until a successful condition is determined by using a pass/fail threshold metric stored in the database as the criteria, the successful condition being present when one of the analogous entries retrieved from the historical medical image database passes the threshold metric.

15. The method of claim 14, further comprising:
comparing all analogous entries in the historical medical image database to the medical image under test; and
when all comparisons have not passed the criteria of the pass/fail threshold metrics stored in the historical medical image database, visually presenting the medical image under test on a user interface with status information showing that no comparative match was found in the historical medical image database.

16. The method of claim 14, further comprising refining the anomaly delineation by reducing a size of the virtual container and repeating the step of incrementally moving it across the medical image under test and determining specific metrics at each position.

17. The method of claim 16, further comprising creating a results tracking map which increments and records a count of a number of occurrences at each image position that the position was within the reduced size virtual container.

18. The method of claim 17, further comprising creating a contour map of the results tracking map on a display by drawing concentric rings around the entries with the largest counts.

19. The method of claim 18, further comprising:
overlaying the contour map on top of the medical image under test to highlight the anomaly; and
visually presenting the medical image under test with the overlaid contour map on a display device.

20. The method of claim 19, further comprising visually presenting on the display device additional information from the database related to the historical reference entry used, the additional information being selected from a group consisting of patient age, patient sex, area of anomaly, shape of anomaly, diagnostic tests performed and their reports, diagnosis/prognosis, treatment, outcome and time to resolution.

21. The method of claim 20, further comprising displaying information recommending or not recommending additional specific medical test procedures to further diagnose a suspected anomaly in the test image, if suggested by historical data of the matched anomaly in the database.

22. The method of claim 21, further comprising displaying a reference to any other anomaly in the database that the present reference anomaly is linked to and recommending medical testing for the linked anomaly.

23. The method of claim 10, further comprising determining the metrics from the historical medical image based upon manual delineations of the anomalies and the virtual container is adjusted to be of the same shape, but five percent smaller than the manual delineation.

24. The method of claim 23, further comprising incrementally moving the virtual container around an area within ten percent of the manual delineation and the specific metrics are determined at each of a plurality of positions to which the virtual container is moved.

25. The method of claim 24, further comprising comparing, using a processor, the metrics of the medical image under test to the specific metrics stored for each analogous entry in the database and a pass/fail threshold is a metric stored in the database.

26. The method of claim 25, further comprising:
comparing all analogous entries in the database to the medical image under test; and
when all metrics have 'failed' as determined by using a pass/fail threshold metrics stored in the database, visually presenting the medical image under test on a user interface with status information showing that no comparative match was found in the database.

27. The method of claim 1, further comprising:
enabling a test operator to confirmed an anomalous object in the medical image under test; and
after such confirmation, modifying the database to include the plurality of determined metrics from the medical image under test as a new set of metrics associated with the medical image under test and confirmation of the anomalous object as an anomaly.

28. A system for analyzing a medical image, comprising:
a database containing sets of a plurality of specific metrics, each of the sets of metrics being derived from an anomaly or a non-anomalous region in an associated one of a plurality of historical medical images such that at least one set is derived from an anomaly of an associated historical medical image and at least one set is derived from a non-anomalous region of an associated historical medical image, each of the metrics in each set of metrics being a different measurement of the associated historical medical image;
a medical imaging device that obtains a medical image under test for analysis;
a processor coupled to said database and said medical imaging device, said processor being configured to determine the plurality of specific metrics from the medical image under test obtained by said medical imaging device, each of the determined metrics being a different measurement of the obtained medical image, said processor being configured to compare the plurality of determined metrics from the medical image under test to the sets of the plurality of metrics from said database to determine a degree of similarity therebetween, the comparison performed by said processor comprising a comparison of each of the determined metrics from the medical image under test to a respective one of the metrics of the retrieved at least one set of the plurality of metrics from said database, said processor being further configured to create a contour map based on the determined degree of similarity between the plurality of determined metrics from the medical image under test and the retrieved at least one set of the plurality of metrics from said database; and
a display device coupled to said processor, said display device being directed by said processor to display the created contour map on the medical image under test.

29. The system of claim 28, further comprising at least one user interface coupled to said processor to enable a user to delineate regions of the medical image under test, said processor being configured to determine the plurality of specific metrics for each delineated region of the medical image under test and then compare the plurality of metrics from each delineated region of the medical image under test to the sets of the plurality of metrics from said database to determine a degree of similarity therebetween.

30. A computer program embodied in non-transitory computer readable media and executed by a processor, the computer program being configured to cause the processor to:
interact with a medical imaging device to obtain a medical image under test to be analyzed;
access a database containing sets of a plurality of specific metrics to enable retrieval of one or more of sets of the plurality of specific metrics, each of the sets of metrics being derived from an anomaly or a non-anomalous region in an associated one of a plurality of historical medical images such that at least one set is derived from an anomaly of an associated historical medical image and at least one set is derived from a non-anomalous region of an associated historical medical image;
direct a processor to determine the plurality of specific metrics from the obtained medical image under test, each of the determined metrics being a different measurement of the obtained medical image;
direct the processor to compare the plurality of determined metrics from the medical image under test to each retrieved set of the plurality of specific metrics from the database to determine a degree of similarity therebetween, the comparison performed by the processor comprising a comparison of each of the determined metrics from the medical image under test to a respective one of the metrics of the retrieved at least one set of the plurality of metrics from the database;

direct the processor to create a contour map based on the determined degree of similarity between the plurality of determined metrics from the medical image under test and the retrieved at least one set of the plurality of metrics from said database; and direct a display device to display the created contour map on the medical image under test.

31. A system for analyzing a medical image, comprising:

a database containing sets of a plurality of specific metrics derived from both anomalies and non-anomalous regions in a plurality of historical medical images, wherein the anomalies and non-anomalous regions are considered to be "good" or normal;

a second database containing sets of a plurality of specific metrics derived from both anomalies and non-anomalous regions in a plurality of historical medical images, wherein the anomalies and non-anomalous regions are considered to be "bad" or abnormal;

a medical imaging device that obtains a medical image under test for analysis;

a processor coupled to said first and second databases and said medical imaging device, said processor being configured to:

determine the plurality of specific metrics from the medical image under test obtained by said medical imaging device, each of the determined metrics being a different measurement of the obtained medical image, compare the plurality of metrics from the medical image under test to the sets of the plurality of metrics from said first database to determine a degree of similarity between the plurality of determined metrics from the medical image under test and each set of the plurality of metrics from said first database, and thereafter and only when the degree of similarity between the plurality of determined metrics from the medical image under test and all of the sets of the plurality of metrics from said first database is below a threshold, compare the plurality of metrics from the medical image under test to the sets of the plurality of metrics from said second database to determine a degree of similarity between the plurality of determined metrics from the medical image under test and each set of the plurality of metrics from said second database, and create a contour map based on the determined degree of similarity between the plurality of metrics from the medical image under test and the sets of the plurality of metrics from said second database; and a display device coupled to said processor, said display device being directed by said processor to display the created contour map on the medical image under test.

32. The system of claim 31, wherein said first database also contains limiting metrics for an allowable size and location of the "good" anomalies.

33. The system of claim 31, wherein said processor and said medical imaging device are physically combined into a homogeneous unit.

* * * * *